United States Patent
French et al.

(10) Patent No.: US 8,585,587 B2
(45) Date of Patent: Nov. 19, 2013

(54) DETERMINING PHASE VARIATION OF LIGHT IN AN ENDOSCOPE

(75) Inventors: Paul Michael William French, Horsted Keynes (GB); Carl Paterson, London (GB); Mark Andrew Aquilla Neil, Botley (GB); Christopher William Dunsby, Leighton Buzzard (GB)

(73) Assignee: Imperial Innovations Limited, London (GB)

( * ) Notice: Subject to any disclaimer, the term of this patent is extended or adjusted under 35 U.S.C. 154(b) by 179 days.

(21) Appl. No.: 13/003,387

(22) PCT Filed: Jul. 9, 2009

(86) PCT No.: PCT/GB2009/001725
§ 371 (c)(1),
(2), (4) Date: Feb. 24, 2011

(87) PCT Pub. No.: WO2010/004297
PCT Pub. Date: Jan. 14, 2010

(65) Prior Publication Data
US 2011/0137126 A1    Jun. 9, 2011

(30) Foreign Application Priority Data

Jul. 10, 2008   (GB) .................................. 0812712.8

(51) Int. Cl.
*A61B 1/07*    (2006.01)
(52) U.S. Cl.
USPC ............................ 600/181; 600/178; 600/182
(58) Field of Classification Search
USPC .......... 600/178, 181, 425, 427, 476–478, 182
See application file for complete search history.

(56) References Cited

U.S. PATENT DOCUMENTS

| 4,937,539 | A | 6/1990 | Grinberg |
| 5,640,267 | A * | 6/1997 | May et al. ..................... 359/322 |
| 5,956,447 | A | 9/1999 | Zel |
| 6,370,422 | B1 | 4/2002 | Richards-Kortum |
| 6,456,769 | B1 * | 9/2002 | Furusawa et al. ............. 385/117 |
| 6,522,407 | B2 * | 2/2003 | Everett et al. ................. 356/369 |
| 6,575,574 | B2 * | 6/2003 | DellaVecchia et al. ....... 351/221 |
| 6,687,010 | B1 * | 2/2004 | Horii et al. .................... 356/479 |
| 6,795,199 | B2 * | 9/2004 | Suhami ......................... 356/601 |

(Continued)

FOREIGN PATENT DOCUMENTS

GB    2275198    8/1994

OTHER PUBLICATIONS

Video-Rate Confocal Endoscopy, T. F. Watson, et al., Journal of Microscopy, vol. 207, Jul. 1, 2002, pp. 37-42.

(Continued)

*Primary Examiner* — John P Leubecker
(74) *Attorney, Agent, or Firm* — Kirschstein et al.

(57) ABSTRACT

An endoscope includes a light source operable to generate coherent incident light, and a plurality of imaging optical fibers that are arranged in a fiber bundle, arranged to receive light at a proximal end of the fiber bundle, and arranged to transmit light to a distal end of the fiber bundle. The endoscope further includes a spatial light phase modulator between the light source and the fiber bundle, and arranged to receive the incident light from the light source and to adjust the relative phase of the incident light entering each of the plurality of imaging optical fibers.

25 Claims, 8 Drawing Sheets

(56) References Cited

U.S. PATENT DOCUMENTS

| | | | |
|---|---|---|---|
| 6,911,637 B1* | 6/2005 | Vorontsov et al. | 250/201.9 |
| 7,235,047 B2* | 6/2007 | MacAulay et al. | 600/182 |
| 7,990,611 B2* | 8/2011 | Betzig | 359/385 |
| 2003/0076571 A1 | 4/2003 | MaCaulay | |
| 2005/0234302 A1* | 10/2005 | MacKinnon et al. | 600/181 |
| 2006/0114473 A1 | 6/2006 | Tearney | |
| 2008/0007733 A1* | 1/2008 | Marks et al. | 356/477 |
| 2008/0049232 A1* | 2/2008 | Vakoc et al. | 356/496 |
| 2009/0021746 A1* | 1/2009 | Toida et al. | 356/484 |

OTHER PUBLICATIONS

Confocal Microscopy Through a Fiber-Optic Imaging Bundle, Arthur F. Gmitro, et al., Optics Letters, vol. 18, Apr. 15, 1993, pp. 565-567.

Fiber-Optic Confocal Microscope: Focon, Tim Dabbs, et al., Applied Optics, vol. 31, No. 16, Jun. 1, 1992.

Optical Coherence Tomography, David Huang, et al., Science, vol. 254, Nov. 22, 1991, pp. 1178-1181.

Optical Coherence Tomography: Introduction, James G. Fujimoto, Marcel Dekker, Inc., ISBN 0-8247-0558-0, 2002, pp. 1-40.

Focal Modulation Microscopy, Nanguang Chen, et al., Optics Express, Nov. 10, 2008, vol. 16, No. 23, pp. 18764-18769.

Aberration-Free Optical Refocusing in High Numerical Aperture Microscopy, Edward J. Botcherby, et al., Optics Letters, Jun. 15, 2007, vol. 32, No. 14, pp. 2007-2009.

Wave-Front Reconstruction From Defocused Images and the Testing of Ground-Based Optical Telescopes, Claude Roddier, et al., Optical Society of America, vol. 10, No. 11, Nov. 1993, pp. 2277-2287.

Wavefront Sensing and the Irradiance Transport Equation, Francois Roddier, et al., Applied Optics, vol. 29, No. 10, Apr. 1, 1990.

Wavefront Sensing, Chapter 5, Principles of Adaptive Optics, R. K. Tyson, Academic Press, New York, 1998, pp. 119-177.

Adaptive Optics in Astronomy, John W. Hardy, Adaptive Optics for Astronomical Telescopes, 1st, Oxford University Press, 1998, pp. 63-65, 154-165.

Demonstration of Closed-Loop Adaptive Optics With a Point-Diffraction Interferometer in Strong Scintillation With Optical Vortices, James Notaras, et al., Optics Express, Oct. 17, 2007, vol. 15, No. 21, pp. 13745-13756.

Instantaneous Phase Measuring Interferometry, R. Smythe, et al., Optical Engineering, Jul./Aug. 1984, vol. 23, No. 4, pp. 361-364.

Digital Holography for Quantitative Phase-Contrast Imaging, Etienne Cuche, et al., Optics Letters, Mar. 1, 1999, vol. 24, No. 5, pp. 291-293.

Two-Dimensional Spatial Light Modulators: A Tutorial, John A. Neff, et al., Proceedings of the IEEE, vol. 78, No. 5, May 1990, pp. 826-855.

Spatial Light Modulators Based on Reflective Micro-Displays, Stefan Osten, et al., Technisches Messen 73, (2006) vol. 3, pp. 149-156.

Spatial Light Modulators: Functional Capabilities, Applications, and Devices, Arthur D. Fisher, International Journal of Optoelectronics, 1990, vol. 5, No. 2, pp. 125-167.

Fluorescence Lifetime Imaging by Asynchronous Pump-Probe Microscopy, C. Y. Dong, et al., Biophysical Journal, vol. 69, Dec. 1995, pp. 2234-2242.

Meadowlark Optics Catalog, pp. 1-56.

* cited by examiner

Wide-field flexible optical endoscope

Fibre bundle microconfocal endoscope

Single mode fibre microconfocal endoscope

Scannerless confocal imaging at the distal end of the fibre bundle

OCT endoscope

"u+v" microconfocal endoscope – where $1/u + 1/v = 1/f$ (a)

(b)

(c)

(a)

(b)

DETERMINING PHASE VARIATION OF LIGHT IN AN ENDOSCOPE

This invention relates to an endoscope.

BACKGROUND TO THE INVENTION

Optical microscopy, and particularly fluorescence microscopy, is a powerful tool in biomedicine and can be applied with exogenous fluorescence labels to study, for example, the distribution of biological components (cells, extracellular matrix material, proteins, metabolites etc.) and their interactions. Biological cells and tissue are themselves fluorescent and this "autofluorescence" signal can also be used to learn about cellular and tissue samples to better understand disease, to study the effect of potential therapeutic agents, and to diagnose disease. Increasingly there is a drive to study molecular biology in vivo in living organisms (e.g. animals) and to gain more information from autofluorescence signals in humans for diagnostic and other applications. Fluorescence microscopes can not only provide intensity-based imaging but can also resolve the fluorescence spectrum and lifetime and polarisation properties. Confocal microscopy provides improved contrast, spatial resolution and optical sectioning compared to wide-field microscopes. Multiphoton microscopes utilise the nonlinear scaling of the excitation process to realise optical sectioning and can confer advantages of reduced photobleaching and reduced attenuation due to absorption and scattering in biological tissue compared to wide-field or confocal microscopes. Unfortunately, the strong optical scattering associated with biological tissue limits the imaging depth of conventional microscopes to typically a few 100 µm. Multiphoton microscopes can image to deeper depths since the longer wavelength excitation radiation experiences reduced attenuation in biological tissue but the imaging depth is still limited to <<1 mm. For these reasons, there is significant interest in using endoscopes to image deeper in biological samples, including animals and humans.

Current endoscopes may be considered in the categories of flexible video endoscopes, rigid optical endoscopes and flexible optical endoscopes. Video endoscopes typically have a miniature CCD camera at the distal end and the flexible section of the endoscope is essentially a cable conduit for the electronic signals and power etc. Video endoscopes are essentially wide-field imaging instruments with an optical performance that can be considered as a wide-field microscope. Rigid optical endoscopes are typically constructed from a series of lenses enclosed in a rigid cylinder and these relay an optical image from the distal to proximal end. They are usually employed as wide-field microscopes with a CCD camera at the proximal end but they can be used in scanning microscope configurations [1] and this approach has recently found favour in multiphoton microscopy where a "stick lens" made from gradient-index ("GRIN") lenses is employed.

Rigid endoscopes are typically used in orthopaedic surgery or surgery in the large body cavities, and for imaging in rodent brains. They are not usually suitable to study internal organs because they are not flexible enough to be passed through internal pathways, small body cavities or vessels in live subjects, and they are typically of limited length. For internal imaging, it is usual to employ flexible endoscopes. For intensity imaging, video endoscopes are most commonly used but for more sophisticated imaging modalities such as hyperspectral imaging or fluorescence lifetime imaging or confocal or multiphoton microscopy (to provide higher resolution and optical sectioning), it is necessary to use a flexible optical endoscope. Flexible optical endoscopes can be divided into wide-field optical endoscopes and microconfocal endoscopes and multiphoton endoscopes.

Wide-field (non-confocal) flexible optical endoscopes typically utilise a fibre bundle to relay the optical image from the sample (distal) end to the detector (proximal) end, as illustrated in FIG. 1(a). These fibre bundles typically comprise ~30,000 optical fibres that each correspond to an image pixel, with the fibre bundle being about 0.6 mm in diameter. This is a small number of pixels compared to a typical CCD camera and so such optical endoscopes offer a smaller number of image resolution elements than video endoscopes or optical microscopes and consequently lower quality images. Cross-talk arising from leakage of light between different optical fibres in the fibre bundle can also degrade the image. The spacing between individual fibre cores (and consequent fill-factor) also impacts the efficiency of light collection and the image quality.

Microconfocal endoscopes either utilise a proximal scanner with an imaging fibre bundle (FIG. 1(b)) or a distal scanner with a single optical fibre (FIG. 1(c)) to convey the light from the sample to the (proximal) detector. In the former case, the fibre bundle can be an array of single mode fibre "cores" that are fabricated together to form a "coherent" bundle.

For the fibre bundle-based microconfocal endoscope [2], the scanner at the proximal end (FIG. 1(b)) scans the excitation beam across the proximal end of the fibre bundle, addressing each optical fibre core sequentially, and the output at the distal end is relayed by the objective lens to scan a focussed beam across the sample. The resulting fluorescence (or reflected light) is imaged back to the same fibre core and the image of the sample is thus relayed to the proximal end of the fibre bundle. This can be imaged directly, e.g. using a CCD, or propagated back through the scanning system to a single detector that records the pixel information sequentially. As with the wide-field endoscope, the limited number of fibre cores in the imaging bundle limits the image quality. When imaging in scattering media such as biological tissue, there can be cross-talk arising from light collected by other fibre cores than the one addressed by the scanner. There can also be leakage of light between the single mode fibres that can contribute to cross-talk. Each single mode fibre core acts as a "confocal pinhole" (and an additional confocal pinhole may also be deployed in front of the detector), leading to optical sectioning and improved resolution and contrast compared to wide-field imaging. Focus adjustment or axial (depth scanning) may be realised by translating the objective lens assembly relative to the distal end of the fibre.

The single mode optical fibre microconfocal endoscope represented in FIG. 1(c) employs a scanner at the distal end, e.g. [3]. The excitation light emerges from the distal end of the single mode fibre, which here serves as the "confocal pinhole". Given the nature and applications of endoscopy, the components at the distal end are required to be small, and so considerable effort has been invested in developing miniature optical scanners. These can be based on microfabricated scanning mirrors or on vibrating fibre tip designs. To date miniaturisation has permitted endoscopes with diameters of a few mm to be developed, but this is still too large for some desired purposes. In general, the fibre-bundle microconfocal endoscope, which does not require a distal (x-y) scanner, can be made thinner than the single mode fibre/distal scanner approach, making it potentially more flexible and able to pass through thinner cavities or vessels etc.

Both the fibre bundle and single fibre approaches to microconfocal endoscopy can be adapted to multiphoton imaging, which can offer deeper penetration in biological tissue.

Unfortunately, since the single mode fibre (or fibre core in the bundle) acts as the confocal pinhole, this removes one of the advantages of multiphoton endoscopy—namely that the confocal pinhole is not needed (since all multiphoton excited photons should originate from the focus) and in scattering media an open pinhole permits more signal to be collected. One way round this for the fibre bundle approach would be to use a large area detector in place of the CCD camera indicated in FIG. 1(b) although the single mode fibre cores would still act as apertures and not collect all of the multiphoton excited fluorescence.

To summarise, microconfocal (and multiphoton) endoscopes offer significant advantages over wide-field endoscopes (video or flexible optical fibre bundle) including optical sectioning (and therefore subsurface imaging), superior image contrast (S/N) and improved lateral resolution. The fibre bundle approach suffers from reduced image quality due to the limited number of pixels, which is a consequence of the number of single mode fibre cores in available fibre bundles and the spacing between the fibre cores. This results in undersampling of the image and the limited fill-factor also impacts light collection efficiency. Cross-talk between different fibre cores—and that arising from any light entering the bundle between the fibre cores—can also be an issue. The single fibre/distal scanner approach can provide a high resolution (fully sampled) image but the size of the scanner means that it is difficult to make a very thin endoscope with this approach. For both approaches a z-position/focussing adjustment usually requires moving parts at the distal end. Multiphoton endoscopy is usually implemented via the single fibre/distal scanner approach, for which the restriction to the fixed pinhole of the optical fibre is a drawback when imaging in scattering media, although this drawback can be mitigated by the use of specially designed fibres such as conventional or microstructured double clad fibres.

There is therefore a desire to reduce the components used at the distal end of the endoscope. In particular, it would be desirable to achieve the (fully sampled image) performance of the distal scanner approach, but without the need for a distal scanner, thereby permitting thinner and more compact endoscopes. For the same reasons, it would also be beneficial to be able to manage without an objective lens at the distal end of the endoscope. It would also be desirable to be able to use fewer fibres in the fibre bundle, in order to be able to reduce the diameter of the fibre bundle and increase its flexibility.

SUMMARY OF THE INVENTION

According to a first aspect of the present invention there is provided an endoscope comprising: a light source operable to generate coherent incident light; and a plurality of imaging optical fibres arranged in a fibre bundle, arranged to receive light at a proximal end of the fibre bundle and to transmit light to a distal end of the fibre bundle; wherein the endoscope further comprises a spatial light phase modulator (often abbreviated to SLPM herein) between the light source and the fibre bundle, the spatial light phase modulator being arranged to receive incident light from the light source and to adjust the relative phase of the incident light entering each of the plurality of imaging optical fibres. The relative phase of the incident light entering each of the fibres is preferably adjusted by the spatial light phase modulator on an individual-fibre basis, with the spatial light phase modulator addressing each fibre individually.

By adjusting the relative phase of the incident light entering each of the plurality of imaging optical fibres, the spatial light phase modulator (at the proximal end of the fibre bundle) enables optical wavefronts emerging from the distal end of the fibre bundle to be synthesised, controlled and scanned.

Various examples of synthesised wavefronts are given below. Since the phase imparted to the light emerging from each of the fibres in the fibre bundle can be adjusted using the spatial light phase modulator to scan the beam, a distal scanner is not required, thereby enabling the number of components at the distal end of the endoscope to be reduced, and thus thinner endoscopes to be realised. Additionally, since focused emerging beams may be synthesised, the objective lens at the distal end of the endoscope may be dispensed with (although in some embodiments it may still be employed). Furthermore, the scanning and focusing abilities made possible by the spatial light phase modulator may enable fewer fibres to be used in the fibre bundle, thereby enabling the diameter of the fibre bundle to be reduced and its flexibility increased.

Optional features are defined herein.

Thus, the endoscope may further comprise a beam splitter arranged between the light source and the spatial light phase modulator, for directing reflected light or fluorescence light to a detector.

The endoscope may further comprise a confocal aperture before the detector in order to realise optical sectioning and other advantages associated with confocal microscopy.

The endoscope may further comprise a second spatial light phase modulator between the beam splitter and the detector. This is advantageous for confocal fluorescence imaging, since the wavelength of the fluorescence light is different from the illumination light.

The spatial light phase modulator may be operable to synthesise a planar wavefront emerging from the distal end of the fibre bundle.

In addition, or alternatively, the spatial light phase modulator may be operable to synthesise a tilted wavefront emerging from the distal end of the fibre bundle. By varying the angle and direction of the synthesised wavefront the beam may be scanned across an object under investigation.

In addition, or alternatively, the spatial light phase modulator may be operable to synthesise a curved wavefront emerging from the distal end of the fibre bundle. By varying the degree of curvature of the synthesised wavefront the focussing of the beam may be adjusted. Thus it may be possible to dispense with the objective lens at the distal end of the endoscope.

The endoscope may further comprise an optical reference arm at the proximal end of the apparatus to permit interferometric detection of the light returning from the sample. The optical path length of the reference arm may be adjustable, e.g. by providing an adjustable mirror at the end of the reference arm. This enables the endoscope to be applied to optical coherence tomography, which is a well-known coherent imaging technique for application in turbid media [4, 5].

Since the individual light rays transmitted along the respective optical fibres in the fibre bundle may suffer from pathlength variations, the endoscope may further comprise means for determining the phase variation of the light transmitted by the fibre bundle by measuring or monitoring the phase variation of reflected light or fluorescence light to produce signals representative of the phase variation, and means for feeding said signals back to the spatial light phase modulator (which may be computer controlled), the spatial light phase modulator being adapted to compensate for such phase variations on preferably an individual-fibre basis. Such measurements may be made continuously or intermittently and may be interleaved with the image acquisition or undertaken as part of an imaging protocol.

The means for determining the phase variation may comprise a wavefront sensor and/or an interferometer. This interferometer could utilise the incident (excitation) radiation reflected from the distal end of the fibre bundle or it could utilize radiation at a different wavelength. It may be necessary to introduce an additional beamsplitter into the beam path for this interferometer. In the latter case a special coating may be applied to the distal tip of the fibre bundle to provide an increased reflection at the said different wavelength and it may be necessary for additional dichroic filters to be included in the beam path.

It may be advantageous to utilize a coherence-gated interferometer that could be configured to select radiation reflected back from the distal end of the fibre bundle. In such a case, the reference arm of the interferometer may comprise a matched length of optical fibre with a mirror at its distal tip. This reference arm optical fibre may be arranged alongside the imaging fibre bundle or integrated in the imaging fibre bundle, so as to experience similar environmental perturbations. A coherence-gated interferometer is particularly applicable if multiphoton excitation is being employed, as the excitation source would already provide broad bandwidth radiation of low temporal coherence.

The endoscope may further comprise beam scanning and/or focussing means at the proximal end of the fibre bundle. This may improve the transverse and/or axial scanning speed of the endoscope.

The endoscope may further comprise spatial light amplitude modulation means. The use of spatial light amplitude modulation means gives further freedom in the synthesis of wavefronts and for engineering the focal intensity distribution in the image, and enables the light fraction directed into the cladding of the fibre bundle to be reduced.

Beneficially, the spatial light phase modulator may be operable to apply phase compensation to compensate for spherical or other aberrations.

In another embodiment, the endoscope may be operable to apply focal modulation microscopy [6, 7] by applying a temporally modulated phase difference to the light transmitted along different subsets of the imaging optical fibres. The phase modulation required for focal modulation imaging may be performed by the said spatial light phase modulator, or a separate spatial light phase modulator.

The light source may be a laser. Moreover, the light source may be an ultrashort pulsed laser, and the detector may be arranged to provide time-correlated single photon counting detection, or some other means of time-resolved detection, thus enabling the endoscope to be applied to fluorescence lifetime imaging.

The endoscope may further comprise a polarising filter at the distal end of the fibre bundle.

The plurality of imaging optical fibres may be arranged in an irregular array in the fibre bundle, in order to reduce the size of unwanted side-lobes on the point spread function of the light emerging from the distal end of the fibre bundle.

According to a second aspect of the present invention there is provided an endoscope comprising: a light source operable to generate coherent incident light; and one or more multimode optical fibres arranged to receive light at a proximal end of the fibre(s) and to transmit light to a distal end of the fibre(s); wherein the endoscope further comprises a spatial light phase modulator between the light source and the fibre(s), the spatial light phase modulator being arranged to receive incident light from the light source and to adjust the relative phase of the incident light entering each of the modes of the fibre(s). Thus, the fibre bundle of the first aspect of the invention is effectively replaced by one or more multimode fibres.

The optional or preferable features described herein in connection with the first aspect of the invention are equally applicable to the second aspect of the invention, as those skilled in the art will readily appreciate.

The endoscope may further comprise spatial light amplitude modulation means for adjusting the amplitude of the incident light entering each of the modes of the fibre(s).

With respect to the first or second aspects of the invention, the endoscope may be adapted to provide spectrally resolved imaging. In addition, or alternatively, the endoscope may be adapted to provide polarisation-resolved imaging, in order to map out the polarisation properties of a sample such as molecular orientation and birefringence. In further embodiments, the endoscope may be adapted to provide a combination of different imaging techniques, e.g. spectrally resolved and time resolved imaging, or temporally resolved and polarisation resolved imaging.

BRIEF DESCRIPTION OF THE DRAWINGS

Embodiments of the invention will now be described, by way of example only, and with reference to the drawings in which.

In the figures, like elements are indicated by like reference numerals throughout. Components illustrated with dashed outlines are optional and may be omitted, or included as required.

DETAILED DESCRIPTION OF PREFERRED EMBODIMENTS

The present embodiments represent the best ways known to the applicants of putting the invention into practice. However, they are not the only ways in which this can be achieved.

Embodiments of the present invention seek to address one or more of the disadvantages mentioned above, essentially providing the (fully sampled image) performance of the distal scanner approach, but without the need for a distal scanner, thereby permitting thinner endoscopes. Embodiments of the present invention may also provide for more efficient collection of scattered fluorescence in a multiphoton endoscope, and may enable fewer fibres to be used in the fibre bundle, thus enabling the diameter of the fibre bundle to be reduced (potentially to a diameter of the order of 0.1 mm, which would be suitable for exploratory use in breast ducts) and its flexibility to be increased.

In essence, the embodiments of the invention combine a "coherent" fibre bundle with spatial light modulator technology at the proximal end of the bundle, in order to allow full synthesis of optical wavefronts at the distal end. The spatial light modulator technology enables two important functions. The first is to correct for the phase and optical path variations between different fibres of the bundle, thereby creating a "phase-correct" optical relay. The second is then to synthesise, modulate and control the wavefronts produced at the distal end of the fibre bundle. This opens up a range of capabilities and offers significant advantages over existing endoscopes including:

(1) Beam scanning at the object without a distal scanner.
(2) Reduction in size and complexity of the distal end allowing for smaller endoscopes.
(3) Engineering the point spread function (PSF) of the illumination (including spatio-temporal modulation).
(4) Adaptive correction of both object and instrument induced aberrations.
(5) Application to coherent imaging techniques.

Figure 1:
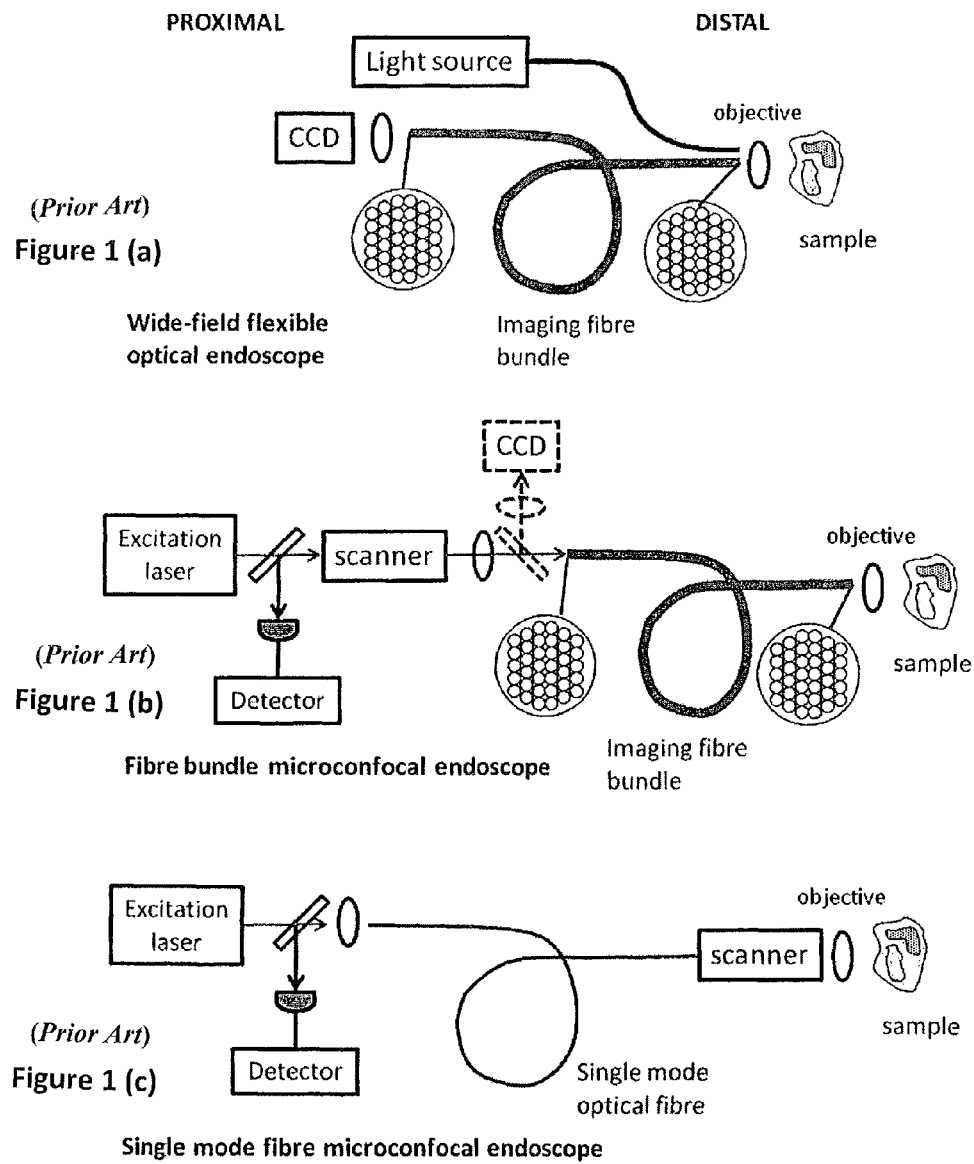
FIG. 1(a), FIG. 1(b) and FIG. 1(c) respectively illustrate examples of prior art endoscope configurations, namely a wide-field flexible optical endoscope, a fibre bundle microconfocal endoscope, and a single mode fibre microconfocal endoscope.
Figure 2:
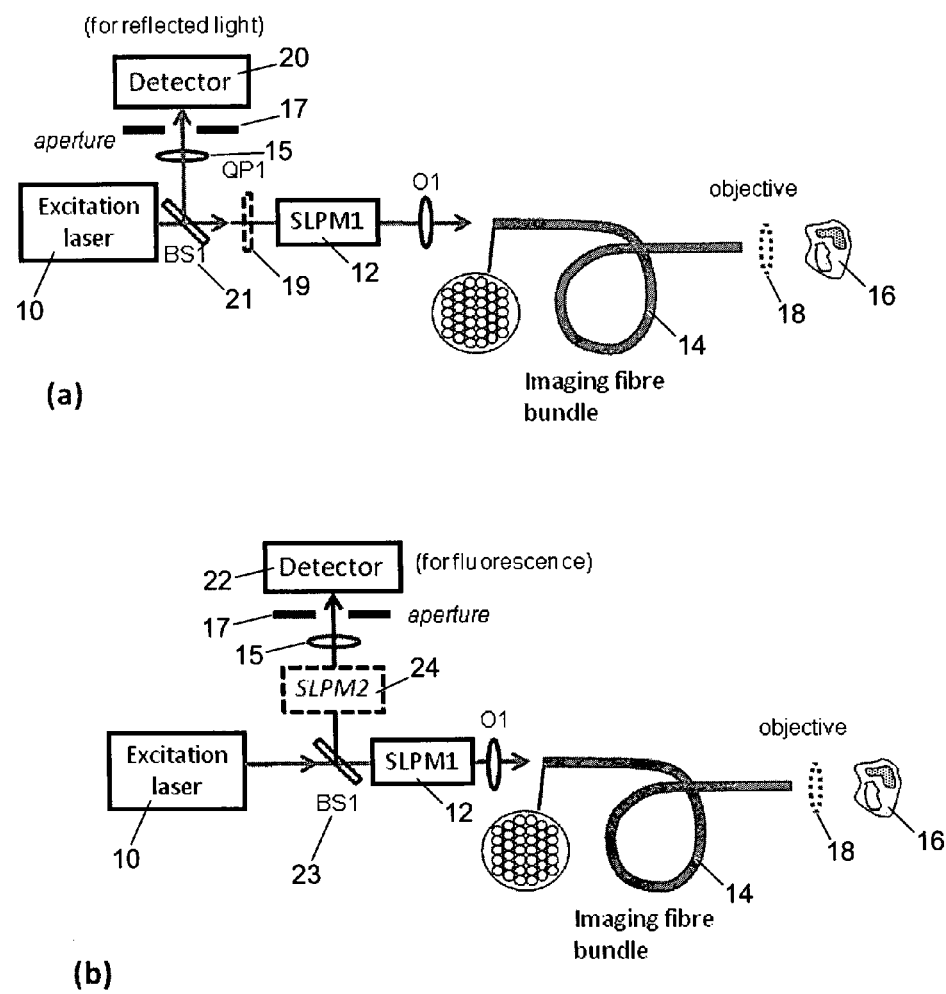
FIG. 2(a), FIG. 2(b) and FIG. 2(c) respectively illustrate a scannerless fibre bundle microconfocal endoscope according to embodiments of the invention, with the configuration of FIG. 2(a) being for use with reflected (or back-scattered) light, the configuration of FIG. 2(b) being for use for confocal fluorescence imaging, and the configuration of FIG. 2(c) being for multiphoton fluorescence imaging.
Figure 2:
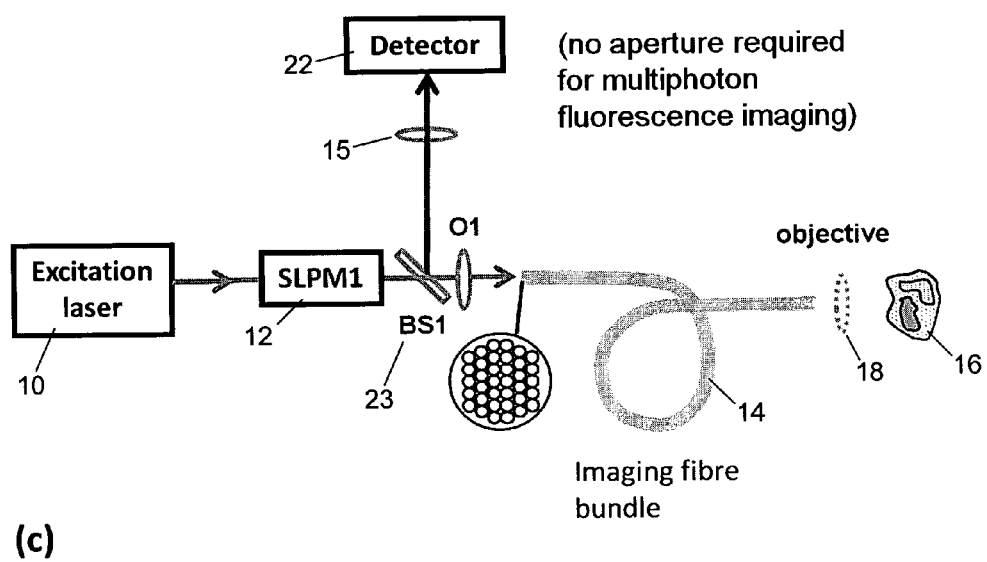

All of these have important implications for a wide range of imaging modalities including confocal, multi-photon, fluorescence, optical coherence tomography and polarization imaging techniques. FIG. 2 shows schematic diagrams of embodiments of the proposed invention for microconfocal endoscopic imaging with reflected light (FIG. 2(a)) and fluorescence light (FIGS. 2(b) and 2(c)).

1. Transverse Scanning with No Distal Scanner (No Moving Parts)

Embodiments of the invention aim to provide fully sampled images in a microconfocal endoscope with no distal scanner. As shown in FIG. 2, the embodiments use spatially coherent illumination generated by an excitation laser 10, and incorporate an imaging fibre bundle 14 with a spatial light phase modulator (SLPM1) 12 at the proximal end to adjust the relative phase of the light emerging from the distal end of the fibres. The coherent light emerging from the distal end of the imaging fibre bundle 14 can, by appropriate adjustment of the relative phase of the light in each fibre core, be made to constructively interfere to create a region of high intensity at the focus of the objective. This is equivalent to synthesising a plane wave emerging at the distal end of the fibre that would be focussed to a point by the objective lens. It is also possible to synthesise a tilted wavefront at the distal end of the fibre, which would result in the light focussing to a different point in the objective focal plane. Thus, by varying the angle and direction of the synthesised tilted wavefront, it is possible to scan the focussed light over the sample 16 in the focal plane of the objective, as sketched in FIG. 3(a). In this way, an effective scanning function is realised without the need for a distal scanner, and the width of the endoscope is limited only by the width of the imaging fibre bundle 14 and the objective lens 18 (if indeed an objective lens 18 is used at all, as discussed further below). The concept of synthesising wavefronts from arrays of coherent sources with appropriate phase differences is analogous to phased array radar techniques.

2. Transverse Scanning with No Distal Scanner or Objective Lens

With an appropriate SLPM 12 it is also possible to synthesise a curved wavefront at the distal end of the imaging fibre bundle 14. This may be used to focus the light without the need for an objective lens 18 at the distal end, as indicated in FIG. 3(b), thus further relaxing the limitations on how thin an endoscope can be constructed.

3. Z (Focus) Adjustments with No Moving Parts

By varying the degree of curvature of the synthesised wavefront emerging from the distal end of the fibre bundle 14, it is possible to adjust the effective focal length, as indicated in FIG. 3(c). Thus the imaging depth, i.e. the distance from the distal end of the fibre bundle 14 at which the light is focussed, may be adjusted. This approach of adjusting the curvature and tilt of the wavefront at the distal end of the fibre bundle may be employed with or without an objective lens 18, to adjust the z-position of the sample plane to be imaged.

The use of an objective lens 18 may be favourable in some situations, e.g. to facilitate the collection of reflected light or fluorescence, and in terms of relaxing the requirements of the phase distribution to be generated by the SLPM 12.

Recently a new technique for adjusting the focal plane of a microscope by translating a mirror at the focus of a second objective has been demonstrated [8]. This could also be utilised with a proximal set-up including a second objective and moving mirror.

4. Implementation

Correcting Phase (Pathlength) Variations Across the Fibre Bundle

It is often thought to be impractical to transmit coherent signals through imaging fibre bundles because of the unknown variation in pathlength (and therefore phase) between different fibre cores and the possibility of these variations changing as the fibre bundle is moved or bent or undergoes strain or temperature changes. The power of the technique proposed here is that the SLPM can compensate for these variations in accumulated phase delay across the single mode cores in the imaging fibre bundle.

If a suitable error signal could be identified, e.g. the intensity of multiphoton excited fluorescence, then an iterative approach to optimising the imaging could be devised that could adaptively optimise the SLPM settings to compensate for any (dynamic) phase variations across the fibre bundle.

Alternatively, the appropriate settings of the SLPM could be determined by monitoring or measuring the spatial phase variation of a fraction of the incident (excitation) light reflected back from the distal end of the imaging fibre bundle, e.g. using an interferometric or wavefront sensing technique. The monitoring or measuring apparatus may be arranged to produce signals representative of the phase variation, and to feed these signals back to the spatial light phase modulator, which may be computer controlled. This adaptive correction may be able to compensate unwanted phase variations "on the fly".

Figure 7:
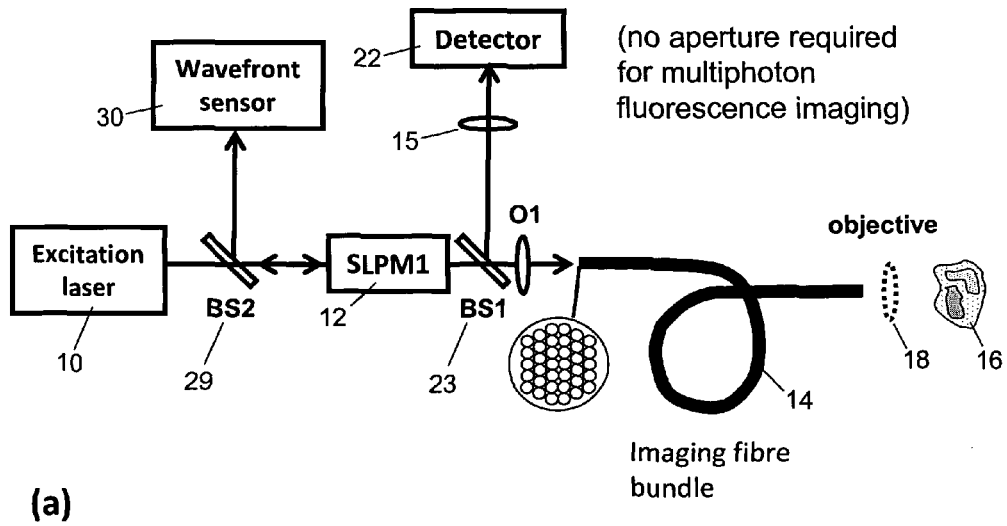
FIG. 7(a) and FIG. 7(b) illustrate methods for measuring the phase variation across the fibre bundle using a wavefront sensor.
Figure 7:
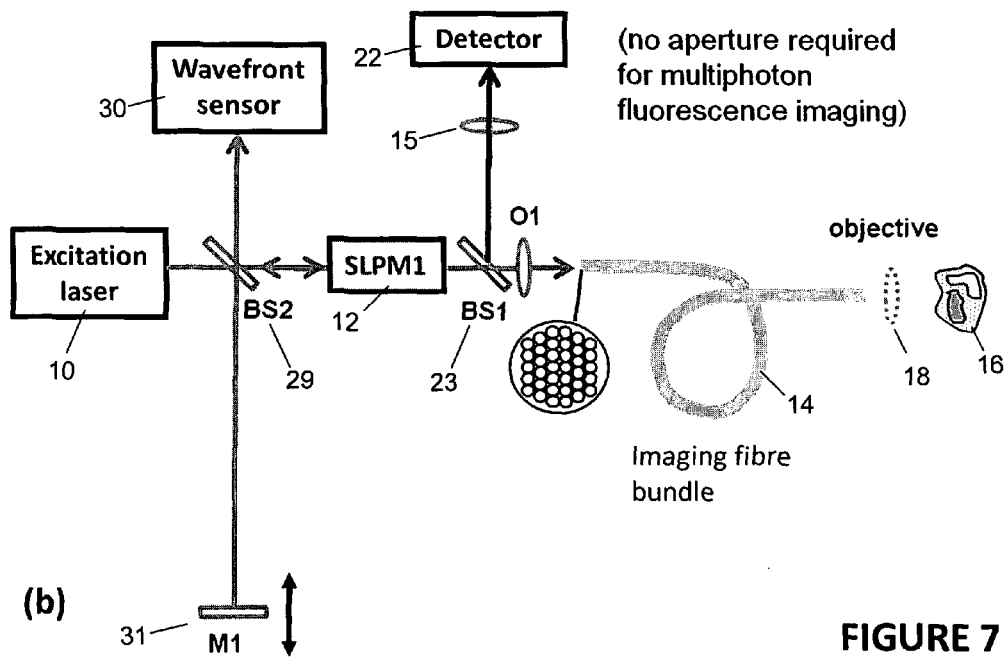

There are a number of possible ways of implementing this, some of which are represented in FIG. 7, which illustrates methods for measuring the phase variation across the fibre bundle using a wavefront sensor. These are illustrated for the case of multiphoton fluorescence endoscopy represented in FIG. 2(c) but could also be implemented with reflected light endoscopy (FIG. 2(a)) or confocal fluorescence endoscopy (FIG. 2(b)). For fluorescence endoscopy it can be convenient to measure the phase variations of the excitation light reflected from the distal end of the fibre, as represented in FIG. 7, but similar measurements could be made of the phase of the fluorescence light or of light from one or more lasers at a different wavelengths to the excitation laser reflected from the distal face of the fibre bundle. FIG. 7(a) represents a possible configuration using a wavefront sensor that does not require a reference arm, whereas FIG. 7(b) represents a configuration when using a wavefront sensor that does require a reference arm to facilitate interferometric measurements.

Thus, as shown in FIG. 7, a wavefront sensor 30 may, for example, be used to measure phase variations arising from small changes in optical path length in the fibre bundle, in order to provide the required information for the spatial light phase modulator. To measure the phase variation of the light transmitted by the fibre bundle, this wavefront sensor 30 could utilise the incident (excitation) radiation reflected from the distal end of the fibre bundle, or potentially light reflected back from some other part of the optical system at the distal end. Moreover, it could utilise radiation at one or more different wavelengths, which could be provided by additional lasers operating at different wavelengths to the excitation source. An additional beamsplitter BS2 29 would be required to direct some of the light back reflected from the distal end of the fibre bundle to the wavefront sensor 30.

In situations where it might be preferable to use radiation at a different wavelength for this measurement of the phase delay variation across the fibre bundle, a special optical coating could be applied to the distal end of the fibre bundle that would transmit the incident (excitation) radiation and the desired fluorescence but would increase the reflectance of the radiation to be used for the measurement of the variation in phase delay across the fibre bundle. For measuring path length changes using a different wavelength, additional dichroic filters may be included in the beam path.

The variation in phase of the reflected light could be measured, for example, using a wavefront sensor 30, such as a curvature wavefront sensor [9], or using phase retrieval from transport of intensity based methods [10], or a pyramid wavefront sensing, or a Shack-Hartmann or any other wavefront sensor known to those skilled in the technique of wavefront sensing [11]. The variation in phase of the reflected light could also be measured using using a lateral shearing interferometer [12], or a point diffraction interferometer [13], or a phase-stepping interferometer, e.g. [14], or using digital holography, e.g. [15].

For the wavefront sensing, lateral shearing and point-diffraction interferometric approaches the phase variation can be measured using back-reflected light from the distal end of the fibre or from the object and/or fluorescent light from the object. Measuring the phase variation after the return has passed through the SLPM (as represented in FIG. 7) allows for closed-loop adaptive control of the SLPM. Broadband radiation or multiple wavelengths can be used to avoid $2\pi$-phase ambiguities in the measured wavefront phase. A separate reference arm is not required for these approaches but one can be used to facilitate coherence gated measurements that can offer enhanced measurement precision.

The phase stepping interferometer and digital holography approaches require a reference arm to form the measurement interferometer, as represented between the beamsplitter BS2 29 and the mirror M1 31 in FIG. 7(b). The interferometric measurement could be implemented with short coherence length radiation so as to preferentially select the light reflected from the distal end of the fibre bundle by interfering it with radiation reflected in a reference arm of the same optical path length as the fibre bundle arm of the interferometer. For multiphoton endoscopy, the excitation radiation would inherently exhibit a short coherence length. The reference arm of the interferometer may contain an optical fibre with a mirror M1 31 at its distal tip and its length matched to that of the fibre bundle. In some embodiments, a reference arm fibre may be arranged alongside the imaging fibre bundle or integrated in the imaging fibre bundle, so as to experience environmental perturbations similar to those experienced by the imaging fibre bundle. The reference arm may also contain a means to adjust the dispersion (i.e. variation of optical pathlength with wavelength) in order to balance the dispersion in each arm of the interferometer, which improves the maximum interferometric sensitivity. For phase-stepping interferometry-based techniques, the SLPM could be used to apply the required phase changes.

In other implementations of interferometric measurement of the phase profile across the fibre bundle, radiation with a long coherence length could be used. This would relax the requirements for a reference arm with an optical pathlength matched to that of the fibre bundle.

Fibre Bundle Geometry

Normally a synthesized approximation to a plane wave emerging from the distal end of the fibre bundle would be focussed to a spot with "side lobes" around it. This light distribution, which can be described as the "point spread function", corresponds to the Fourier transform of the spatial profile of the fibre bundle. If a fibre bundle with an irregular array of fibre cores was to be used, rather than the type normally used in endoscope systems where the fibre cores are spaced on a hexagonal array, then the size of the unwanted side-lobes on the point spread function (and therefore the focussed spot at the sample) could be reduced.

It may be possible to use a single multimode fibre in place of the fibre bundle, in which case the SLPM would adjust the phase and amplitude of the light coupled into different modes of the multimode fibre. Furthermore, a plurality of multimode fibres could be used.

Polarisation Issues

In general, polarisation dispersion (where the polarisation of the radiation changes during propagation through the fibre bundle) will be an issue since it can result in phase variations in the light emerging from the fibre bundle. To some extent this may be mitigated by using fibre bundles with polarisation-preserving fibre structures. The SLPM1, or an assembly of several spatial light modulators, may also be able to compensate for phase changes arising from polarisation effects as well as from other effects, e.g. which change the effective optical path length. By dynamically measuring the phase profile of the light emerging from the fibre bundle as discussed above, it may be possible to "adaptively" compensate for polarisation and other effects "on the fly". One approach could be to place a polariser at the distal end of the fibre and use proximal amplitude modulation as well as phase modulation to adjust the synthesised waves emerging from the distal end of the fibre bundle.

As discussed below, manipulating the polarisation properties of the endoscope may permit optical properties of the sample, e.g. birefringence, to be studied.

Use of Proximal Scanner as Well as SLPM1

While the SLPM1 can, in principle, provide the transverse scanning capability, this can be rather slow compared to the galvanometric scanning mirrors used in most confocal microscopes, or to other types of beam scanner such as acousto-optic scanners or electro-optic scanners. For some implementations, it may therefore be preferable to also incorporate a proximal galvanometric mirror scanner, or other type of beam scanner, to be used in conjunction with the SLPM1. In this situation the main function of the SPLM would be to adjust the phase profile of the synthesised wavefronts emerging from the distal end of the fibre bundle in order to maintain and control the focussing of the excitation beam.

Use of Proximal Focussing as Well as SLPM1

While the SLPM1 can, in principle, provide the focusing (axial scanning) capability, this may be rather slow compared to some other focussing mechanisms, including motorised or piezoelectric actuators, used in confocal microscopes or other instruments. For some implementations, it may therefore be preferable to also incorporate a proximal focussing mechanism to be used in conjunction with the SLPM1.

Type of SLPM

Spatial light modulators are well-known optical components that are able to apply spatially varying modulation of the phase and or amplitude and or polarisation of an incident light field [16, 17, 18, 19].

In general, SLPM1 should be a spatial light phase modulator (spatial light pathlength modulator) although it may also be useful to be able to modulate amplitude too (using a spatial light amplitude modulator, or "SLAM"), which will give further freedom in the synthesis of wavefronts and for engineering the focal intensity distribution in the image. A further reason to utilise a spatial light amplitude modulator function would be to reduce the light fraction directed into the cladding of the fibre bundle (i.e. the SLAM could ensure all the light is directed into the fibre cores).

Optical Configuration

Figure 3:
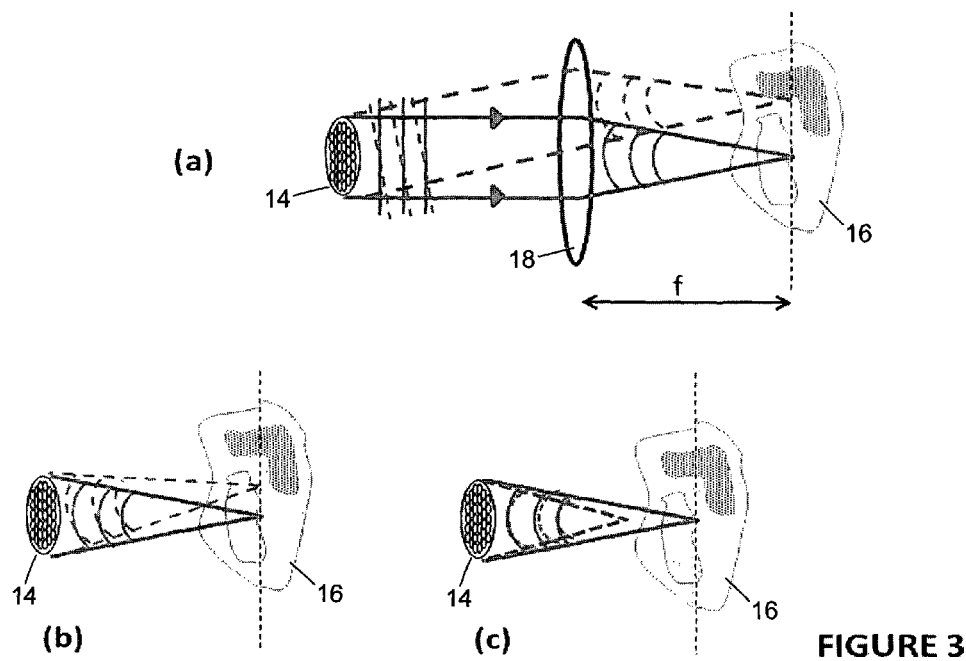
FIG. 3(a), FIG. 3(b) and FIG. 3(c) respectively illustrate examples of synthesised wavefronts and focusing arrangements at the distal end of a fibre bundle.
Figure 4:
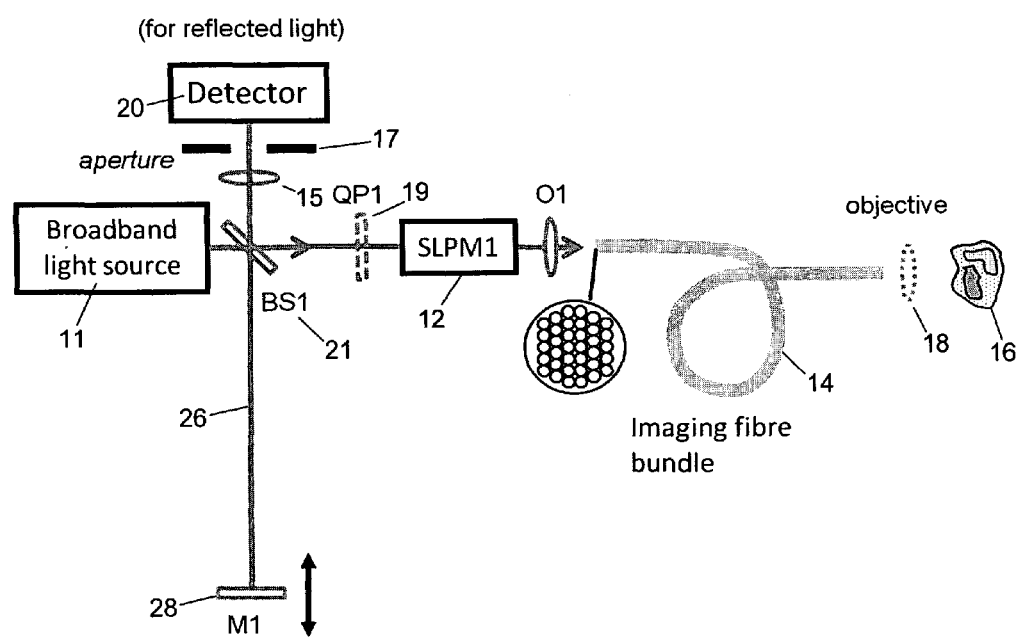
FIG. 4 illustrates the addition of a optical reference arm with an adjustable mirror to a scannerless fibre bundle microconfocal endoscope using reflected light, to enable optical coherence tomography (OCT)
Figure 5:
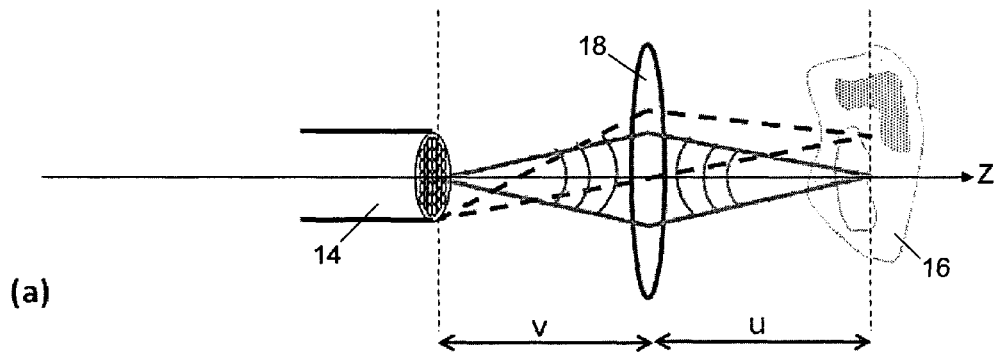
FIG. 5(a), FIG. 5(b) and FIG. 5(c) and FIG. 6(a) and FIG. 6(b) illustrate embodiments of "u+v" imaging configurations.
Figure 5:
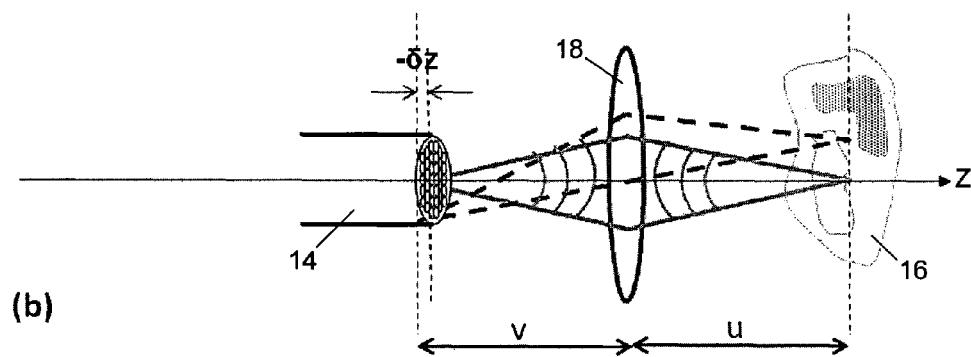
Figure 5:
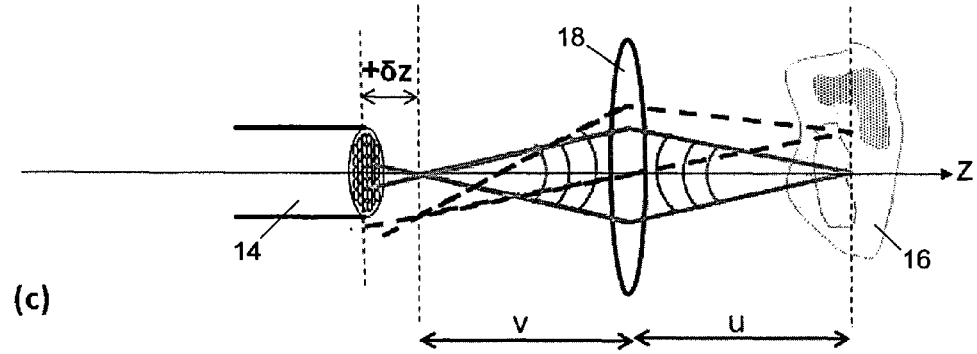
Figure 6:
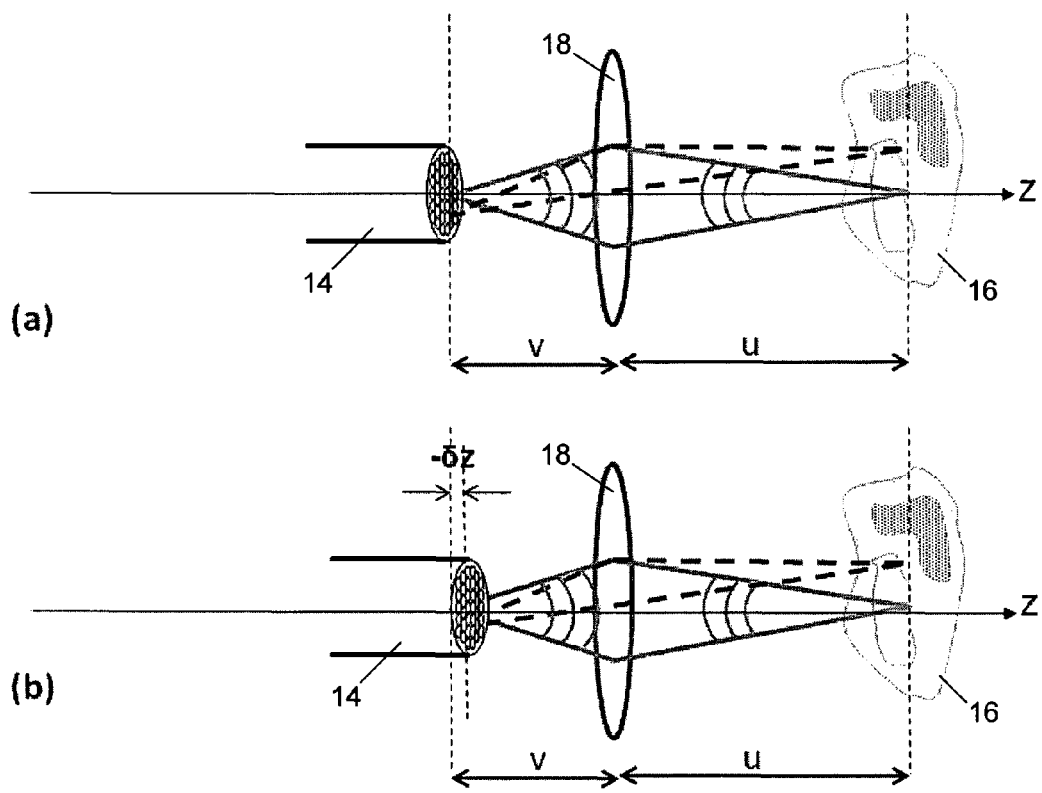

FIGS. 1 to 7 are schematics only and specific implementations may involve a number of optical components or subsystems that would be straightforward for a person skilled in the art to design. For example, the component labelled as O1 in FIGS. 2 to 4 is an optical system to relay the light from the spatial light modulator to the entrance face of the fibre bundle. In some configurations this could be a lens, and in others it could be a number of lenses or mirrors.

The optical system, O1, could be used to relay the light from SLPM1 such that a plane wave is synthesised at the output (distal) end of the fibre bundle or it could do some of the focussing such that a converging (focussing) wave could be synthesised at the distal end of the fibre bundle. In some configurations this would relax the constraints on the performance of SLPM1. In general, the functions of SLPM1 and O1 should be considered together.

5. Improved Collection for Multiphoton Imaging in Scattering Media

The system outlined above could be adapted for multiphoton imaging. It has the advantage that fluorescence could be collected by all the fibre cores in the imaging fibre bundle— thereby potentially improving the collection efficiency compared to the single mode fibre-distal scanner approach. The relative improvement would depend on the numerical aperture (NA) of the imaging fibre bundle cores and the corresponding single mode fibre, as well as on the scattering properties of the sample. For multiphoton microscopy, the second spatial light phase modulator (SLPM2) and the detector aperture would not be needed since all detected florescence photons contribute to useful signal.

6. Implementation of Confocal Detection

For multiphoton fluorescence imaging, all detected fluorescence should originate from the focus of the objective and so no confocal detection pinhole is necessary. For confocal imaging a detection pinhole is required to realise optical sectioning and the other advantages associated with confocal microscopy. With the arrangement shown in FIG. 2(a), the array of single mode fibre cores will have a limited numerical aperture and so the fibre bundle may, to some extent, preferentially transmit rays emanating from points on the focal plane. This could provide a degree of confocal detection but it is likely that an aperture will need to be employed in front of the detector at the proximal end, for which phase-corrected imaging through the bundle will permit confocal imaging.

For reflected light (elastic scattering), as shown in FIG. 2(a), the phase changes experienced upon return through the fibre bundle 14 could again be compensated by the same spatial light phase modulator (SLPM1) 12 and a lens 15 could focus the detected light though a confocal aperture 17 in front of the detector 20. The beamsplitter 21 could be one that transmits a fraction of the light and reflects the rest (e.g. a 50/50 or 30/70 beamsplitter). It could also be a polarising beam splitter used in conjunction with a quarter wave phase retardation plate 19 as indicated in FIG. 2(a). In this standard arrangement, polarised illumination light passes through the polarising beam splitter 21 with minimal loss and the reflected light has its polarisation rotated by 90 degrees such that it is reflected by the polarising beamsplitter 21 with minimal loss. In some arrangements, it may be possible to use the SLPM1 12 to also serve as the quarter wave plate. In further configurations, it is possible to use appropriate phase retardation optics (or appropriate settings of SLPM1) to analyse the polarisation state of the reflected light and so map the polarisation properties of the sample.

This scannerless microconfocal endoscope could also be used for optical coherence tomography, as discussed in section 7 below.

For confocal fluorescence imaging, as shown in FIG. 2(b), a dichroic beamsplitter 23 directs the fluorescence light to the detector 22. Since this may include unwanted "out-of-plane" fluorescence, a lens 15 and confocal aperture 17 at the detector 22 may be used to reject this light. Since the wavelength of the fluorescence is different from the illumination, a second spatial light phase modulator (SLPM2) 24 may be used to correct for dispersion/phase distortions experienced by the fluorescence while propagating back through the fibre bundle 14, and the lens 15 can then focus the fluorescence light though the confocal aperture 17 in front of the detector 22.

7. Application to Optical Coherence Tomography (OCT)

OCT [9] is a combination of low coherence interferometry and confocal microscopy that is sometimes implemented in endoscope configurations and usually requires some form of scanner to acquire images. Embodiments of the invention described here can be adapted to OCT by incorporating a source 11 of broadband (short coherence length) but spatially coherent radiation, such as a femtosecond laser or a superluminescent diode, and a reference arm 26 as shown in FIG. 4. Coherence gating is used to acquire images using only light from the sample 16 that is coherent with that from the reference arm 26. Using a light source of short coherence length, this means that the depth of the image plane in the sample is such that the reflected (backscattered) light propagates for the same optical pathlength as the light in the reference arm 26. The imaging depth can therefore be adjusted by translating the reference arm mirror (M1) 28, while the SLPM 12 can be used to scan the focussed beam along one axis (for "A scan" imaging) or along two axes for "en face" OCT. BS1 21 may be a polarising beam splitter, in which case a quarter wave plate should be added in the reference arm 26, and also a means to adjust the polarisation of the input laser 10. Alternatively, BS1 21 may be a regular amplitude dividing beamsplitter, in which case quarter wave plate QP1 19 would not be required. Optionally, a fibre of similar type and length as those used in the imaging fibre bundle 14 can be incorporated in the reference arm 26 to compensate for group velocity dispersion in the bundle. Alternatively, another means could be introduced for adjusting the dispersion of the reference arm in order to match the dispersion in each arm of the interferometer, which improves the maximum interferometric sensitivity.

8. Potential for Correcting Aberrations Using SLPM

There can be significant spherical and other aberrations when imaging in biological tissue. By adjusting the SLPM 12, it may be possible to compensate for aberrations, which is important when imaging at high numerical aperture. If the aberration is known, then the phase compensation required can be calculated and programmed into the SLPM settings. Adaptive compensation is also possible, for which a feedback (error) signal is required so that the system can iterate to an optimum setting. For multiphoton fluorescence imaging, it is often sufficient to maximise the fluorescence signal, although care must be taken not to change the imaging depth when optimising the applied SLPM phase values to compensate for aberrations. An alternative approach is to analyse some quality of the recorded image and iteratively adjust the applied SLPM phase values to maximise this. One example is to maximise the width of the spatial frequency spectrum of the image [10]. Adaptive phase compensation could also be applied to remove variations in phase between light travelling through different single mode cores in the imaging fibre bundle.

9. "u+v" Detection Configurations

The ability to adjust the focussing of the light emerging from the fibre bundle 14 by adjusting the phase using SLPM1 12 permits the detected light to be collected in a "u+v" imaging configuration (where 1/u+1/v=1/f in the usual way), as shown in FIG. 5(a). If the SLPM1 12 is set to direct light to each fibre core individually (as was the case for the known configuration depicted in FIG. 1(b)) then it can be focussed, e.g. at a distance 2 f, in front of the objective lens, and any reflected or fluorescence light from this point in the sample will be imaged back to a point at the fibre bundle. For this set-up, depicted in FIG. 5(a), the end of the fibre bundle 14 is in a conjugate image plane to the (sample) plane. This configuration using a single fibre core at a time does not require "phase-correct" imaging through the fibre bundle 14 and is already an established technique. However, illuminating multiple fibre cores and correcting for the phase or optical path variations across the fibre bundle 14, as proposed herein, opens up new possibilities by allowing the outgoing wave to be synthesised from multiple fibres in the bundle 14, permitting the emerging wavefront to be controlled. This may be implemented by illuminating multiple fibre cores and by "defocusing" the arrangement shown in FIGS. 1(b) and 5(a), for example by translating the end of the fibre bundle with respect to the objective lens, as shown in FIGS. 5(b) and 5(c). It would be possible to adjust the setting of the SLPM1 12 such that the forward propagating (excitation) light could still be focussed, e.g. near 2f, in front of the objective lens. This approach could have the advantage that the reflected/detected signal would be captured by multiple fibre cores, but a thinner fibre bundle could be used to efficiently capture light collected by the objective, compared to the situation of FIG. 3. It could also be advantageous to have the end of the fibre bundle 14 located away from an image plane for the purposes of manipulating the spatial wavefront of the light, e.g. for compensating for aberrations.

In general, the degree to which the distal end of the fibre bundle is translated away from the image plane (where 1/u+1/v=1/f) will have implications for the performance and requirements of the spatial light modulator (e.g. SLPM1) and the degree of spatial control offered. It will also have implications for light collection and spatial resolution:

Distal end of fibre bundle in image plane (1/u+1/v=1/f):
The intensity in the object focal plane is an image of that at the end of the fibre bundle and so amplitude control alone can be used to steer the beam. Amplitude and phase control can be used to adjust the focus of the beam.
Distal end of fibre bundle in pupil (Fourier) plane (u≈v=f):
The intensity at the object focal plane is formed from the outputs of all the fibres. Phase control alone is necessary to focus and steer the beam. This configuration offers maximum complexity in the control of the beam since all fibres are used simultaneously.
Distal end of fibre bundle in intermediate plane "near focus":
This configuration offers reduced complexity in the control of the beam compared with the pupil plane configuration. The number of fibres contributing to the focus in the object at any one time depends on the proximity of the distal end to the focal plane, which can be used to adjust the trade off between simplicity of control and degree of complexity in the synthesized wavefronts.

The "u+v" arrangement can also be configured to provide magnification, i.e. u≠v and magnification=v/u. This allows both control of the field of view and the spatial resolution while allowing the divergence at the exit of the single mode fibres to be matched with the required numerical aperture of the light at the object to optimize light collection efficiency. Again, translating the fibre bundle 14 out of the image plane, as shown in FIG. 6(b), can impact the resolution, light collection efficiency and the requirements for the spatial light modulator.

10. Improving Performance, Particularly in Scattering Media, Using Focal Modulation Imaging When imaging in scattering media such as biological tissue, the imaging performance of confocal and multiphoton microscopy is compromised. For multiphoton microscopy the main limitation is associated with the ability to achieve sufficiently high excitation intensities in the focal plane to generate a useful detectable level of multiphoton excited fluorescence. Scattering and absorption both reduce the intensity at the focus. For confocal microscopy, the scattering not only reduces the excitation intensity at the focus, it also leads to scattered photons originating outside the focal volume being scattered into trajectories that pass through the confocal pinhole and therefore degrade the S/N of the detected signal.

At the BiOS 2008 meeting in San Jose, USA, a presentation by Chen et al [6] presented a technique they called Focal Modulation Microscopy, which has subsequently been published in Optics Express [7]. This technique employed a phase modulator to sinusoidally modulate half the spatial extent of the excitation beam such that the intensity in the focal volume was modulated at the same frequency. This modulated excitation focus therefore results in a modulated fluorescence signal from the focal volume—but, in principle, fluorescence excited "out-of-plane" should not be modulated. Synchronous detection should therefore preferentially select fluorescence originating from the confocal volume and this can serve as an effective "confocal filter". This technique could be exploited using the new microconfocal endoscope proposed here. The synchronous detection provides more sensitive detection, which could be useful for both multiphoton and single photon microconfocal confocal endoscopes. For the single photon microconfocal endoscope, it would also be useful in the absence of scattering media since it would provide an effective confocal filter—perhaps permitting the second SLPM and detector pinhole to be omitted. Focal plane modulation could be straightforwardly implemented by modulating a subset of the pixels of the SLPM or by using a separate phase modulator to specifically modulate a (spatial) fraction of the beam.

The use of demodulated detection to preferentially select light from the excitation focus was previously demonstrated by Dong et al. in 1995 [20] in a technique they described as asynchronous pump probe fluorescence microscopy where two excitation beams at slightly different pulse repetition rates were focussed to the same focal volume and the correlation signal was detected at the difference frequency.

11. Fluorescence Lifetime Imaging, Spectrally-Resolved and Polarisation-Resolved Imaging This new proposed microconfocal endoscope can be straightforwardly applied to fluorescence lifetime imaging (FLIM) if an ultrashort pulsed excitation laser is used with a time-resolved detection technique such as time-correlated single photon counting (TCSPC) detection. Frequency domain techniques may also be used, in which the phase and modulation depth of the fluorescence is compared to that of a modulated excitation signal. This could be conveniently combined with the focal plane modulation technique.

This proposed new approach to multiphoton and microconfocal endoscopy should be applicable to any spectrally resolved imaging technique that is applicable to multiphoton or confocal microscopy.

While this technique can be applied to polarisation-resolved microscopy, there is a possibility that the polarisation could be altered in an unpredictable manner by propagation through the fibre bundle. This could be addressed by the use of a polarising filter at the distal end of the fibre bundle but this could lead to variations in transmitted intensity that, in turn could be corrected using an appropriate spatial light modulator arrangement at the proximal end.

REFERENCES

[1] T. F. Watson et al, J. Micros. 207 (2002) 37
[2] A. F. Gmitro and D. Aziz, Opt. Lett. 18 (1993) 565
[3] T. Dabbs and M. Glass, Appl. Opt. 31 (1992) 3030
[4] D. Huang, E. A. Swanson, et al., Science 254 (1991) 1178
[5] Handbook of Optical Coherence Tomography, edited by Brett E. Bouma, Guillermo J. Tearney, (Marcel Dekker, Inc), ISBN 0-8247-0558-0, 2002.
[6] NanGuang Chen, Chee-Howe Wong, Colin J. R. Sheppard, National Univ. of Singapore (Singapore), Focal modulation microscopy, paper [6861-16]
[7] N. Chen et al, Opt Expr. 16, (2008) 18764
[8] Botcherby et al., Opt. Lett. 32 (2007) 2007
[9] C. Roddier and F. Roddier, J. Opt. Soc. Am. A v10, p 2277 (1993)
[10] F. Roddier, Appl. Opt. v29, 1402-1403 (1990)
[11] R. K. Tyson "Principles of Adaptive Optics", (Academic Press, New York, 1998)
[12] John W. Hardy, Adaptive Optics for Astronomical Telescopes, 1st, Oxford University Press, 1998
[13] J. Notaras and C. Paterson, Opt Express, 15, (2007) 13745
[14] R. Smythe and R. Moore, "Instantaneous phase measuring interferometry," Opt. Eng. 23, (1984) 361-364
[15] E. Cuche et al., Optics Lett. 24 (1999) 291
[16] U. Efron, editor. Spatial light modulator technology Material, devices and applications. Marcel Dekker, Inc, 1994.
[17] J. A. Neff, R. A. Athale, and S. H. Lee. Two-dimensional spatial light modulators: a tutorial. Proceedings of the IEEE, 78 (1990) 826
[18] S. Osten, S. Kruger, and A. Steinhoff. Spatial light modulators based on reflective micro-displays. Technisches messen, 73 (2006) 149
[19] Spatial light modulators: Functional capabilities, applications, and devices. Fisher, A. D., International Journal of Optoelectronics. 5 (1990) 125
[20] C. Y. Dong et al., Biophys. J. 69 (1995) 2234

The invention claimed is:
1. An endoscope, comprising:
a light source operable to generate coherent incident light;
a plurality of imaging optical fibers arranged in a fiber bundle, and arranged to receive light at a proximal end of the fiber bundle and to transmit light to a distal end of the fiber bundle; and
a spatial light phase modulator between the light source and the fiber bundle, the spatial light phase modulator being arranged to receive incident light from the light source and to adjust the relative phase of the incident light entering each of the plurality of imaging optical fibers,
the spatial light phase modulator being operable to synthesize a tilted wavefront emerging from the distal end of the fiber bundle, and to vary the angle and direction of the synthesized wavefront and thereby scan the light,
the spatial light phase modulator being operable to synthesize a curved wavefront emerging from the distal end of the fiber bundle, and to vary the degree of curvature of the synthesized wavefront and thereby adjust its focussing;
means for determining the phase variation of the light transmitted by the fiber bundle by measuring or monitoring the phase variation of reflected light or fluorescence light to produce signals representative of the phase variation; and
means for feeding said signals back to the spatial light phase modulator,
the spatial light phase modulator being adapted to compensate for the phase variation.

2. The endoscope as claimed in claim 1, further comprising a beam splitter arranged between the light source and the spatial light phase modulator, for directing the reflected light or fluorescence light to a detector.

3. The endoscope as claimed in claim 2, further comprising a confocal aperture before the detector.

4. The endoscope as claimed in claim 3, further comprising a second spatial light phase modulator between the beam splitter and the detector.

5. The endoscope as claimed in claim 2, having no objective lens at the distal end of the fiber bundle.

6. The endoscope as claimed in claim 1, further comprising an objective lens at the distal end of the fiber bundle.

7. The endoscope as claimed in claim 1, wherein the spatial light phase modulator is operable to synthesize a planar wavefront emerging from the distal end of the fiber bundle.

8. The endoscope as claimed in claim 1, further comprising an optical reference arm at the proximal end of the apparatus; and wherein the optical path length of the reference arm is adjustable.

9. The endoscope as claimed in claim 1, wherein the means for determining the phase variation comprise one of a wavefront sensor and an interferometer.

10. The endoscope as claimed in claim 9, wherein the interferometer is a coherence-gated interferometer.

11. The endoscope as claimed in claim 10, wherein the interferometer has a reference arm that comprises a matched length of optical fiber with a mirror at its distal tip.

12. The endoscope as claimed in claim 11, wherein the matched length of optical fiber is arranged alongside the imaging fiber bundle or is integrated in the imaging fiber bundle.

13. The endoscope as claimed in claim 1, arranged to use radiation at a different wavelength for the measurement of the phase variation across the fiber bundle.

14. The endoscope as claimed in claim 13, further comprising a coating applied to the distal tip of the fiber bundle to provide an increased reflection at the said different wavelength.

15. The endoscope as claimed in claim 1, further comprising means for beam scanning at the proximal end of the fiber bundle.

16. The endoscope as claimed in claim 1, further comprising means for beam focussing at the proximal end of the fiber bundle.

17. The endoscope as claimed in claim 1, further comprising means for spatial light amplitude modulation.

18. The endoscope as claimed in claim 1, wherein the spatial light phase modulator is operable to apply phase compensation to compensate for spherical or other aberrations.

19. The endoscope as claimed in claim 1, operable to apply focal modulation imaging by applying a temporally modulated phase difference to the light transmitted along different subsets of the imaging optical fibers.

20. The endoscope as claimed in claim 19, wherein the phase modulation required for focal modulation imaging is performed by one of the spatial light phase modulator and a separate spatial light phase modulator.

21. The endoscope as claimed in claim 1, wherein the light source is an ultrashort pulsed laser.

22. The endoscope as claimed in claim 21, further comprising a detector arranged to provide time resolved detection, wherein the time resolved detection is time-correlated single photon counting detection.

23. The endoscope as claimed in claim 1, further comprising a polarizing filter at the distal end of the fiber bundle.

24. The endoscope as claimed in claim 1, adapted to provide spectrally resolved imaging; or polarization resolved imaging; or a combination of different imaging techniques.

25. An endoscope, comprising:
a light source operable to generate coherent incident light;
one or more multimode optical fibers arranged to receive light at a proximal end of the fiber(s) and to transmit light to a distal end of the fiber(s);
a spatial light phase modulator between the light source and the fiber(s), the spatial light phase modulator being arranged to receive incident light from the light source and to adjust the relative phase of the incident light entering each of the modes of the fiber(s);
  the spatial light phase modulator being operable to synthesize a tilted wavefront emerging from the distal end of the fiber(s), and to vary the angle and direction of the synthesized wavefront and thereby scan the light, and
  the spatial light phase modulator being operable to synthesize a curved wavefront emerging from the distal end of the fiber(s), and to vary the degree of curvature of the synthesized wavefront and thereby adjust its focussing;
means for determining the phase variation of the light transmitted by the one or more multimode optical fibers by measuring or monitoring the phase variation of reflected light or fluorescence light to produce signals representative of the phase variation; and
means for feeding said signals back to the spatial light phase modulator,
the spatial light phase modulator being adapted to compensate for the phase variation.

* * * * *